(12) United States Patent
McCaughan

(10) Patent No.: US 10,413,570 B2
(45) Date of Patent: Sep. 17, 2019

(54) METHOD OF MANUFACTURING A ZINC COMPOUND LOZENGE

(71) Applicant: Daniel McCaughan, Exton, PA (US)

(72) Inventor: Daniel McCaughan, Exton, PA (US)

(*) Notice: Subject to any disclaimer, the term of this patent is extended or adjusted under 35 U.S.C. 154(b) by 187 days.

(21) Appl. No.: 15/366,211

(22) Filed: Dec. 1, 2016

(65) Prior Publication Data
US 2018/0153933 A1 Jun. 7, 2018

(51) Int. Cl.
*A61K 33/30* (2006.01)
*A61K 9/00* (2006.01)
*A61K 47/18* (2017.01)

(52) U.S. Cl.
CPC ............ *A61K 33/30* (2013.01); *A61K 9/0056* (2013.01); *A61K 47/183* (2013.01)

(58) Field of Classification Search
CPC ..... A61K 33/30; A61K 47/183; A61K 9/0056
USPC ............ 426/3, 660, 74, 658; 424/49, 54, 58; 514/494; 264/299
See application file for complete search history.

(56) References Cited

U.S. PATENT DOCUMENTS

| | | | | |
|---|---|---|---|---|
| 4,684,528 A * | 8/1987 | Godfrey | ................. | A23G 3/368 424/49 |
| 4,758,439 A * | 7/1988 | Godfrey | ................. | A23G 3/368 424/49 |
| 5,897,891 A * | 4/1999 | Godfrey | ................. | A61K 33/34 424/48 |
| 7,547,454 B2 * | 6/2009 | Gupta | ..................... | A61K 8/19 424/642 |
| 2005/0226907 A1 * | 10/2005 | Moneymaker | ......... | A61K 31/00 424/439 |
| 2005/0239763 A1 * | 10/2005 | Motyka | ................ | A61K 31/555 514/184 |
| 2006/0068005 A1 * | 3/2006 | Ross | ..................... | A61K 9/0056 424/464 |
| 2006/0246200 A1 * | 11/2006 | Parvez | ..................... | A23L 2/38 426/590 |
| 2007/0099886 A1 * | 5/2007 | Gupta | ..................... | A61K 8/347 514/184 |
| 2007/0207191 A1 * | 9/2007 | Kanzer | .................... | A61K 9/14 424/449 |
| 2008/0075674 A1 * | 3/2008 | DuPratt | ................ | A61K 9/0058 424/48 |
| 2008/0193602 A1 * | 8/2008 | Moneymaker | ......... | A61K 9/006 426/73 |
| 2009/0317470 A1 * | 12/2009 | Patel | .................... | A61K 9/0056 424/486 |
| 2016/0279056 A1 * | 9/2016 | Zhao | .................... | A61K 9/0056 |
| 2017/0157013 A1 * | 6/2017 | Schaeffer-Korbylo | ...................... | A61K 8/58 |

* cited by examiner

*Primary Examiner* — Nahida Sultana
(74) *Attorney, Agent, or Firm* — The Keith Miller Law Group; Keith Miller

(57) ABSTRACT

The invention described herein is a method for manufacturing a zinc compound lozenge, comprising the steps of adding at least one form of glycine and at least one form of ionic zinc salt to deionized water forming a zinc-glycine mixture; heating the zinc-glycine mixture to a first temperature; heating a stock base material to at least it's melting point; stirring in the zinc-glycine mixture to the stock base material; adding at least one flavor concentrate while stirring thoroughly to create a final mixture; pouring the final mixture into a mold specifying a final shape of the zinc compound lozenge; and cooling the final mixture in the mold until solid.

17 Claims, 2 Drawing Sheets

METHOD OF MANUFACTURING A ZINC COMPOUND LOZENGE

BACKGROUND OF THE INVENTION

Several clinical and medical studies published publicly over the past few years have indicated the possibility of successfully using an oral lozenge of a zinc compound to inhibit and/or deter the development and/or growth of various forms of cancer and precancerous conditions in mammals, particularly humans. However, the efficacy of therapeutic treatments used during the administering of the zinc compound can be compromised by other medical factors when using the traditional method regarding the bio-delivery uptake system of the elemental zinc within the stomach and small intestine.

Research has found that when modest quantities of zinc are slowly ingested by mouth so that the interior surfaces of the mouth and throat are intermittently bathed in a solution of ionic zinc, both the time course and the severity of the symptoms of the precancerous cells, cancerous cells, along with various precancerous and cancerous conditions are remarkably altered in a favorable way. However, it was repeatedly found that the disagreeable taste of the zinc gluconate tablets was a serious problem. Many patients receiving zinc gluconate discontinued the treatment on the first day "due to objection to treatment." It was noted that "the zinc gluconate lozenges [tablets] used caused an unexpected unpalatability and distortion of taste in many subjects . . . " and mentioned "the somewhat bitter aftertaste which some people report for zinc gluconate." Furthermore, "unpalatable taste," "distortion of taste," and "mouth irritation" were common objections.

A problem in the manufacturing of zinc compounds containing other ingredients, such as traditional sweeteners infused in order to make the zinc compound more palatable to the taste, cause the zinc compound to chelate, or bind, the elemental zinc ion to other non-metal ions throughout the bio-delivery process. This chelation, or binding effect, renders the efficacy of the elemental zinc ineffective in these particular subjects by not allowing it to be effectively delivered throughout the body.

Empirical data and research has shown that there is currently no clinically proven therapy to delay or inhibit esophageal cancer progression in the Barrett's esophagus patient. The only approach recommended by the medical community is to observe for appearance of carcinoma. This is done grossly and through histology of randomly taken biopsies. Patients with dysplasia typically undergo mucosal resection or laser ablation of the affected tissue, a procedure with a painful recovery. Improvements in the treatment of Barrett's esophagus and the inhibition of Barrett's esophagus related adenocarcinoma are desired.

In addition to other subjects diagnosed with various forms of cancer or precancerous conditions, subjects diagnosed with Barrett's esophagus would be prime candidates for this alternative treatment using the delivery of an elemental zinc compound incorporating the formulation and compounding as described herein, which allows for the alternate delivery form of zinc into the body as a free radical ion to be absorbed into the body and successfully inhibit, prevent, deter, or otherwise delay and slow the progression and/or growth of cancer and/or precancerous cells within the body.

Accordingly, in order to take advantage of the important effect of zinc upon the precancerous cells, cancerous cells, along with various precancerous and cancerous conditions it is necessary to develop a method of manufacturing a zinc compound lozenge comprised of pharmaceutically acceptable zinc salts which are palatable enough to be taken with the frequency necessary to suppress the symptoms of the precancerous cells, cancerous cells, along with various precancerous and cancerous conditions.

The present invention provides a solution to the aforementioned problems and difficulties in producing a zinc compound lozenge designed to prevent and/or treat cancer or precancerous conditions.

BRIEF SUMMARY OF THE INVENTION

The present invention generally relates to the field of cancer prevention and treatment. More specifically, the present invention relates to the formulations and methods for making zinc compounds and compositions used for the prevention and/or treatment of cancer and/or precancerous conditions.

The present invention describes the formulation and manufacturing of oral zinc supplements. More specifically, the present invention relates to formulating and manufacturing compositions containing a zinc compound lozenge which, when taken orally, provides a palatable lozenge without an undesirable aftertaste. Generally, the composition includes a base material and a select amino acid in addition to the zinc compound. Additionally, the composition containing the zinc compound does not bind, or chelate, the elemental zinc when being delivered into the human body.

DETAILED DESCRIPTION OF THE INVENTION

The following description of the preferred embodiments of the invention is intended to enable someone skilled in the prior art to make and use this invention, but is not intended to limit the invention to these preferred embodiments.

Figure 1:
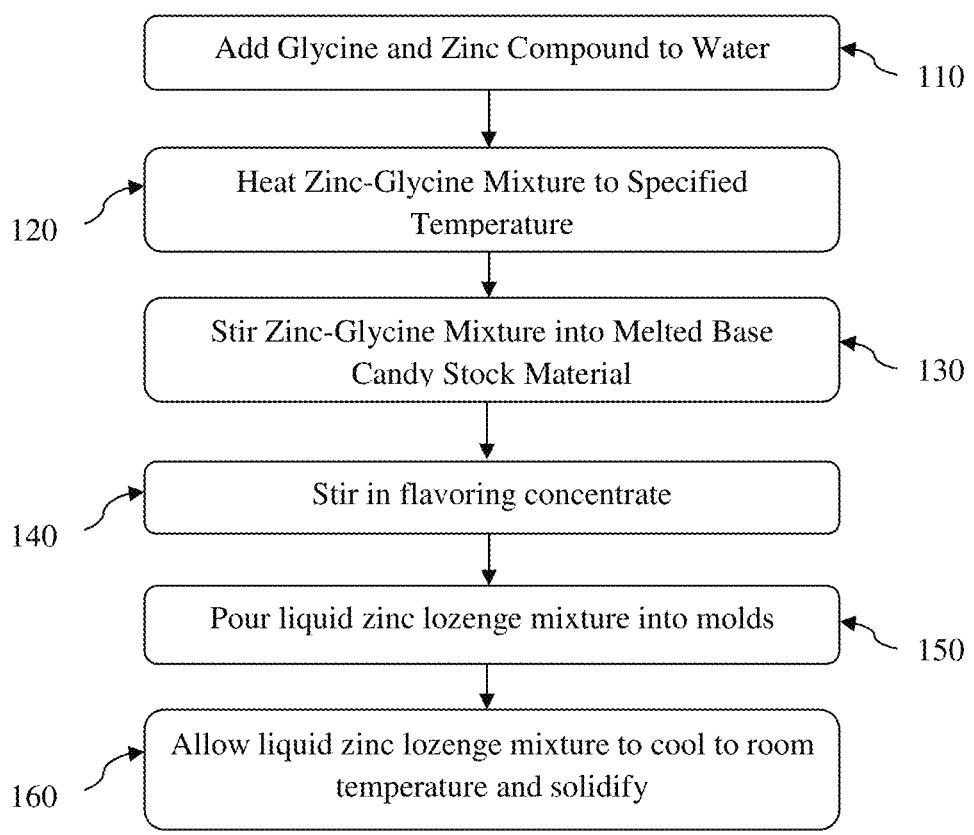
FIG. 1 is a flow chart for a ZINC COMPOUND LOZENGE MANUFACTURING SYSTEM according to a preferred embodiment of the present invention.

Now referring to FIG. 1, the invention described herein is a method for manufacturing a zinc compound lozenge, comprising the steps of adding at least one form of glycine and at least one form of ionic zinc salt to deionized water 110 forming a zinc-glycine mixture; heating the zinc-glycine mixture to a first temperature 120; heating a stock base material to at least it's melting point; stirring in the zinc-glycine mixture to the stock base material 130; adding at least one flavor concentrate while stirring thoroughly to create a final mixture 140; pouring the final mixture into a mold specifying a final shape of the zinc compound lozenge 150; and cooling the final mixture in the mold until solid 160.

In the preferred embodiment, the amino acid glycine is preferably used to manufacture the zinc compound lozenge because glycine is a non-alcohol based sugar. By itself, zinc compounds are non-palatable, so many types of lozenges containing only the ionic zinc salt without the amino acid will not be tolerated in the mouth by the user over time. In other types of lozenges, the amino acids used to make the lozenge more palatable cause the elemental zinc in the ionic zinc salt to be inactive due to the amino acid alcohol-based sugars binding, or chelating, with the elemental zinc molecule. Therefore, the amino acid glycine is preferred because it does not bind, or chelate, to the ionic zinc salt.

However, the amino acid glycine is very difficult to work with. For instance, temperatures during the manufacturing process are critical and must be carefully regulated or else the glycine will burn and become unusable. Also, the temperature gradient must be carefully monitored and handled during the heating and cooling periods. Additionally, maintaining the proper balance of water to glycine is very important because if too much water is added, the temperature will drop and will take longer to heat up again. If too much water evaporates from the mixture, then the glycine will tend to re-crystallize and not stay in a liquid form for proper mixing into the stock base material In the preferred embodiment, the zinc-glycine mixture is preferably prepared using an agitated, steam-jacketed kettle by adding glycine to deionized water first, then adding the ionic zinc salt to the glycine-water mixture, then heating to 190 degrees F. Once the temperature of 190 degrees F. is reached, the zinc-glycine mixture is then transferred, via a pump while maintaining the temperature of the zinc-glycine mixture at precisely 190 degrees F., to a holding kettle that will monitor and maintain the heated temperature while the zinc-glycine mixture is pumped into the cooker with the stock base material. The pumping is performed while maintaining the water/chemical ratio of the zinc-glycine mixture in addition to the temperature. If insufficient water is used, the glycine in the mixture may re-crystallize between the pump and the cooker. Note, also, that the zinc-glycine mixture cannot be over-heated; otherwise the chemicals will begin breaking down due to the excessive heat. Other similar methods not described above may be used without limitation.

The stock candy base material is preferably a hard candy base material manufactured as is typical in the industry. To prepare a hard candy stock base material, a mixture of sucrose, white corn syrup and deionized water is heated to a boiling temperature of 212 degrees F. while stirring. When a clear solution is obtained, the mixture is heated further to 300 degrees F. without stirring at the maximum rate possible without boil-over. The pale straw-colored product is poured in an approximately 4 millimeter layer and allowed to cool to room temperature. Then, the layer is fractured into convenient-sized pieces and stored in a sealed container.

Alternatively preferably, the stock base material may be a soft candy base manufactured as is typical in the industry. The soft candy base material is preferably prepared by combining corn syrup, sucrose, corn starch, flavoring agents, and water. The mixture is then preferably brought to boiling briefly to effect hydration of the corn starch. The resulting candy has the rubbery consistency when it cooled to room temperature. This soft candy base material is then cut into cubes and stored.

In the preferred embodiment, the zinc-glycine mixture is dosed into the cooker with the melted stock base material prior to the final cook via a pump calibrated against the output of the cooker while maintaining a heated temperature of 190 degrees F. The final cook traditional for a candy base with post-cook vacuum is used to remove the added water. Transcendent gradual and radiant cooling and forming is normal for producing a hard candy lozenge product.

The method of manufacture of a zinc compound lozenge formula is preferably made using an advanced swept surface universal-type vacuum batch cooker. The swept surface cooker eliminates the problem of a reaction occurring during cooking between the glycine and the reducing sugars in the hard candy base, or soft candy base, which results in a burn in the cooker over time.

In the preferred embodiment, the zinc compound lozenge produced using this method preferably has a density ranging from 1.3 grams per cubic centimeter to 1.7 grams per cubic centimeter. The zinc compound lozenge may be formed into any shape and size so long as the minimum surface area of the lozenge is approximately 850 square millimeters. Preferably, the total weight of the finished zinc compound lozenge is in a range of 2 grams to 7 grams, where the ideal final weight of the zinc compound lozenge is 4.5 grams.

Figure 2:
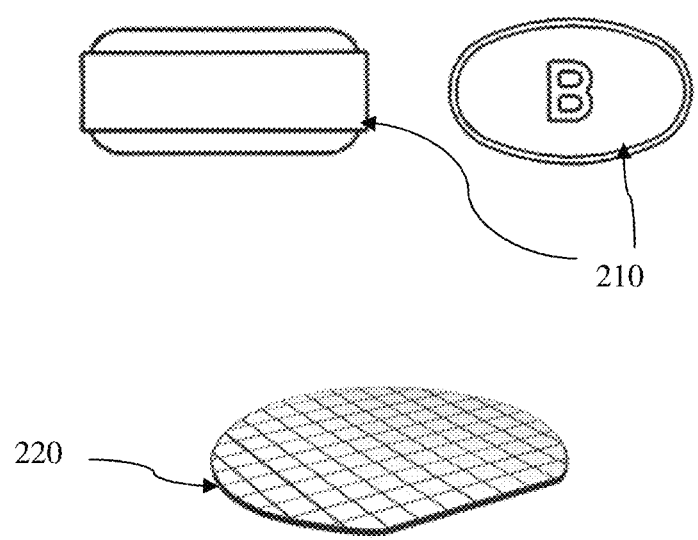
FIG. 2 illustrates examples of the various shapes and sizes for a zinc lozenge per a ZINC COMPOUND LOZENGE MANUFACTURING SYSTEM according to a preferred embodiment of the present invention.

FIG. 2 illustrates examples of different shapes and sizes of the finished zinc compound lozenge including an ellipsoid-shaped lozenge 210, or a thin wafer lozenge 220. The shape and size of the lozenge is structured and arranged such that the lozenge easily dissolves in the mouth and throat, thus releasing the elemental zinc from the ionic zinc salt to be effectively delivered within the human body. The examples provided are not the only shapes and sizes that can be used, other shapes and sizes not outlined herein may be used so long as the minimum surface area and total weight of the finished zinc compound lozenge is within the stated requirements.

The zinc compound lozenge produced using this method preferably contains between 3 milligrams to 22 milligrams of the ionic zinc salt. In another preferred variation, the zinc compound lozenge contains between 6 milligrams to 19 milligrams of the ionic zinc salt. In another preferred variation, the zinc compound lozenge contains between 10 milligrams to 16 milligrams of the ionic zinc salt.

The ionic zinc salts preferably used in this preferred method are commonly found forms such as sulfate, chloride, acetate, gluconate, ascorbate, citrate, aspartate, picolinate, orotate and transferrin salts, as well as zinc oxide and complexes of divalent zinc with associated amino acids. In the preferred embodiment, the zinc gluconate salt is more compatible with the amino acid glycine used. However, other combinations of ionic zinc salts and amino acids may be contemplated.

In an alternate embodiment, the method of manufacture of a zinc compound lozenge comprises the steps of, adding at least one form of glycine to deionized water forming an at least one glycine solution; adding at least one form of ionic zinc salt to said at least one glycine solution creating a zinc-glycine mixture; heating the zinc-glycine mixture to a first temperature; gravity-filtering the at least one zinc-glycine mixture while hot to produce a zinc-glycine filtrate; cooling the zinc-glycine filtrate to a solid state; grinding the zinc-glycine filtrate into a fine powder; heating a stock base material to at least it's melting point; stirring in the zinc-glycine filtrate to the stock base material; adding at least one flavor concentrate while stirring thoroughly to create a final mixture; pouring the final mixture into a mold specifying a final shape of the zinc compound lozenge; and cooling the final mixture in the mold until solid.

In the preferred embodiment, the at least one flavor concentrate is preferably a cherry flavoring. Cherry flavoring is preferably the most effective flavor mask available that allows consumers to find medicinal products palatable. In an alternate embodiment, other flavor concentrates may be used, such as a grape flavoring. In general, citrus-type flavorings, such as lemon, orange and grapefruit flavorings have been found to reduce the medical efficacy of the ionic zinc salt contained in the lozenge.

I claim:

1. A method for manufacturing a zinc compound lozenge, the method comprising:
   adding at least one glycine and then at least one ionic zinc salt to deionized water in a kettle forming a zinc-glycine mixture;
   heating the zinc-glycine mixture to a first temperature;
   heating a stock base material in a cooker to at least it's melting point forming a melted stock base material, wherein the cooker is a swept-surface vacuum batch cooker;
   pumping the zinc-glycine mixture from the kettle to the cooker using a pump calibrated to maintain the first temperature of the zinc-glycine mixture;
   stirring the zinc-glycine mixture into the melted stock base material and cooking to remove added water;
   adding at least one non-citrus flavor concentrate to the cooker while stirring thoroughly to create a final mixture;
   pouring the final mixture into a mold specifying a final shape of the zinc compound lozenge; and
   cooling the final mixture in the mold until solid.

2. The method of manufacturing the zinc compound lozenge of claim 1 wherein a final molecular ratio of the at least one glycine to the at least one ionic zinc salt is in a range of 2:1 to 20:1.

3. The method of manufacturing the zinc compound lozenge of claim 1, further comprising:
   adding the at least one glycine to the deionized water forming an at least one glycine solution;
   adding the at least one ionic zinc salt to the at least one glycine solution creating the zinc-glycine mixture; and
   heating the zinc-glycine mixture to the first temperature.

4. The method of manufacturing the zinc compound lozenge of claim 1, further comprising:
   gravity filtering the zinc-glycine mixture while hot creating a zinc-glycine filtrate;
   allowing the zinc-glycine filtrate to cool forming a solid zinc-glycine filtrate;
   grinding the solid zinc-glycine filtrate into a fine powder; and
   adding the powdered zinc-glycine filtrate to the melted stock base material.

5. The method of manufacturing the zinc compound lozenge of claim 1 wherein the at least one ionic zinc salt is a zinc-gluconate.

6. The method of manufacturing the zinc compound lozenge of claim 5 wherein the zinc-gluconate is combined with an amino acid glycine.

7. The method of manufacturing the zinc compound lozenge of claim 1 wherein the at least one non-citrus flavor concentrate is a cherry flavoring.

8. The method of manufacturing the zinc compound lozenge of claim 1 wherein the at least one ionic zinc salt content is within a range from 3 mg to 22 mg.

9. The method of manufacturing the zinc compound lozenge of claim 1 wherein the first temperature is about 190 degrees F.

10. The method of manufacturing the zinc compound lozenge of claim 1 wherein the stock base material is a hard candy base.

11. The method of manufacturing the zinc compound lozenge of claim 1 wherein the stock base material is a soft candy base.

12. The method of manufacturing the zinc compound lozenge of claim 1 wherein the final shape and size of the zinc lozenge provides a minimum surface area of 850 square millimeters.

13. The method of manufacturing the zinc compound lozenge of claim 1 wherein the zinc lozenge has a density ranging from 1.3 grams per cubic centimeter to 1.7 grams per cubic centimeter.

14. The method of manufacturing the zinc compound lozenge of claim 1 wherein a final weight of the zinc lozenge is within a range of 2 grams to 7 grams.

15. The method of manufacturing the zinc compound lozenge of claim 1 wherein the final shape of the zinc lozenge is an ellipsoid.

16. The method of manufacturing the zinc compound lozenge of claim 1 wherein the final shape of the zinc lozenge is a wafer.

17. A method of manufacturing a non-copper containing zinc compound lozenge, the method comprising:
   adding at least one glycine and then at least one ionic zinc salt to deionized water in a kettle forming a zinc-glycine mixture;
   heating the zinc-glycine mixture to a first temperature;
   heating a stock base material in a cooker to at least it's melting point forming a melted stock base material, wherein the cooker is a swept-surface vacuum batch cooker;
   pumping the zinc-glycine mixture from the kettle to the cooker using a pump calibrated to maintain the first temperature of the zinc-glycine mixture;
   stirring the zinc-glycine mixture into the melted stock base material and cooking to remove added water;
   adding at least one non-citrus flavor concentrate to the cooker while stirring thoroughly to create a final mixture, wherein the final mixture has a uniform amount of the at least one glycine to the at least one ionic zinc salt, and a final molecular ratio of the at least one glycine to the at least one ionic zinc salt is in a range of 2:1 to 20:1;
   pouring the final mixture into a mold specifying a final shape of the zinc compound lozenge; and
   cooling the final mixture in the mold until solid.

* * * * *